United States Patent [19]
Kehoe et al.

[11] Patent Number: 5,700,648
[45] Date of Patent: Dec. 23, 1997

[54] STREPTOLYSIN O ANTIGEN DERIVATIVES, THEIR PRODUCTION AND USES

[76] Inventors: Michael Kehoe, 14 Springhouse Lane, Ebchester, Co Durham DH8 0QF; Michael Pinkney, 6 Ilfracombe Gardens, Whitley Bay, NE26 3SL, both of England

[21] Appl. No.: 296,879

[22] Filed: Aug. 26, 1994

Related U.S. Application Data

[63] Continuation of Ser. No. 959,167, Oct. 9, 1992, abandoned, which is a continuation of Ser. No. 830,549, Jan. 31, 1992, abandoned, which is a continuation of Ser. No. 543,357, Jun. 25, 1990, abandoned.

[51] Int. Cl.$^6$ ............ C07K 14/315; C07K 16/12; C12P 21/02; G01N 33/53
[52] U.S. Cl. ............ 435/7.1; 435/69.3; 530/350; 530/389.5; 530/403; 530/413; 530/806; 530/825
[58] Field of Search ............ 514/12; 530/350, 530/403, 405, 409, 825, 806, 389.5, 413; 424/190.1, 237.1, 244.1, 832; 435/7.1, 69.1, 69.3

[56] References Cited

U.S. PATENT DOCUMENTS

| | | | |
|---|---|---|---|
| 4,508,831 | 4/1985 | Toth | 436/512 |
| 4,517,303 | 5/1985 | Freytag et al. | 930/280 |
| 5,354,846 | 10/1994 | Kehoe | 530/350 |

OTHER PUBLICATIONS

Saunders, et al., *Infection and Immunity* 57, 2547 (Aug., 1989).

Pinkney et al., *Infection and Immunity* 57, 2553 (Aug., 1989).

*Primary Examiner*—Jeffrey E. Russel
*Attorney, Agent, or Firm*—Flehr Hohbach Test Albritton & Herbert, LLP; Walter H. Dreger; Robin M. Silva

[57] ABSTRACT

This application teaches a cytolytic derivative of the thiol-activated protein streptolysin O. The derivatization comprises the deletion of the amino acid cysteine from the amino acid sequence of naturally occurring streptolysin O; and optionally other alterations in said naturally occurring amino acid sequence by amino acid substitution, deletion, inversion, insertion or addition.

16 Claims, 7 Drawing Sheets

FIG. 2A-1

```
         10        20        30        40        50        60
TTATTAGCAAGCTTGCCATTTTATTTAAACCGTCAAAGCATACTAGCTAATATAACCAAA 70        80        90       100       110       120
GCGTTAAAAGATGCGCATTATTAGAGAGGCTATGGCACATTACAAATTAGGAGAATTTGC 130       140       150       160       170       180
TCACTATCAAGATACTATGCTTGATATGGTCGAAAGAACAATAGAAACATTTTAGAATGA 190       200       210       220       230       240
TAAAAAGGTATGAAGGACATGTCTAATAAAAAAACATTTAAAAAATACAGTCGCGTCGCT
                           M  S  N  K  K  T  F  K  K  Y  S  R  V  A 250       260       270       280       290       300
GGGCTACTGACGGCAGCTCTTATCATTGGTAACCTTGTTACTGCTAATGCTGAATCGAAC
 G  L  L  T  A  A  L  I  I  G  N  L  V  T  A  N  A  E  S  N 310       320       330       340       350       360
AAACAAAACACTGCTAGTACAGAAACCACAACGACAAATGAGCAACCAAAGCCAGAAAGT
 K  Q  N  T  A  S  T  E  T  T  T  T  N  E  Q  P  K  P  E  S 370       380       390       400       410       420
AGTGAGCTAACTACTGAAAAAGCAGGTCAGAAAACGGATGATATGCTTAACTCTAACGAT
 S  E  L  T  T  E  K  A  G  Q  K  T  D  D  M  L  N  S  N  D 430       440       450       460       470       480
ATGATTAAGCTTGCTCCCAAAGAAATGCCACTAGAATCTGCAGAAAAAGAAGAAAAAAAG
 M  I  K  L  A  P  K  E  M  P  L  E  S  A  E  K  E  E  K  K 490       500       510       520       530       540
TCAGAAGACAAAAAAAAGAGCGAAGAAGATCACACTGAAGAAATCAATGACAAGATTTAT
 S  E  D  K  K  K  S  E  E  D  H  T  E  E  I  N  D  K  I  Y 550       560       570       580       590       600
TCACTAAATTATAATGAGCTTGAAGTACTTGCTAAAAATGGTGAAACCATTGAAAATTTT
 S  L  N  Y  N  E  L  E  V  L  A  K  N  G  E  T  I  E  N  F 610       620       630       640       650       660
GTTCCTAAAGAAGGCGTTAAGAAAGCTGATAAATTTATTGTCATTGAAAGAAAGAAAAAA
 V  P  K  E  G  V  K  K  A  D  K  F  I  V  I  E  R  K  K  K 670       680       690       700       710       720
AATATCAACACTACACCAGTCGATATTTCCATCATTGACTCTGTCACTGATAGGACCTAT
 N  I  N  T  T  P  V  D  I  S  I  I  D  S  V  T  D  R  T  Y 730       740       750       760       770       780
CCAGCAGCCCTTCAGCTGGCTAATAAAGGTTTTACCGAAAACAAACCAGACGCGGTAGTC
 P  A  A  L  Q  L  A  N  K  G  F  T  E  N  K  P  D  A  V  V
```

FIG 2A-2

```
         790       800       810       820       830       840
ACCAAGCGAAACCCACAAAAAATCCATATTGATTTACCAGGTATGGGAGACAAAGCAACG
 T  K  R  N  P  Q  K  I  H  I  D  L  P  G  M  G  D  K  A  T 850       860       870       880       890       900
GTTGAGGTCAATGACCCTACCTATGCCAATGTTTCAACAGCTATTGATAATCTTGTTAAC
 V  E  V  N  D  P  T  Y  A  N  V  S  T  A  I  D  N  L  V  N 910       920       930       940       950       960
CAATGGCATGATAATTATTCTGGTGGTAATACGCTTCCTGCCAGAACACAATATACTGAA
 Q  W  H  D  N  Y  S  G  G  N  T  L  P  A  R  T  Q  Y  T  E 970       980       990      1000      1010      1020
TCAATGGTATATTCTAAGTCACAGATTGAAGCAGCTCTAAATGTTAATAGCAAAATCTTA
 S  M  V  Y  S  K  S  Q  I  E  A  A  L  N  V  N  S  K  I  L 1030      1040      1050      1060      1070      1080
GATGGTACTTTAGGCATTGATTTCAAGTCGATTTCAAAAGGTGAAAAGAAGGTGATGATT
 D  G  T  L  G  I  D  F  K  S  I  S  K  G  E  K  K  V  M  I 1090      1100      1110      1120      1130      1140
GCAGCATACAAGCAAATTTTTTACACCGTATCAGCAAACCTTCCTAATAATCCTGCGGAT
 A  A  Y  K  Q  I  F  Y  T  V  S  A  N  L  P  N  N  P  A  D 1150      1160      1170      1180      1190      1200
GTGTTTGATAAATCAGTGACCTTTAAAGAGTTGCAACGAAAAGGTGTCAGCAATGAAGCT
 V  F  D  K  S  V  T  F  K  E  L  Q  R  K  G  V  S  N  E  A 1210      1220      1230      1240      1250      1260
CCGCCACTCTTTGTGAGTAACGTAGCCTATGGTCGAACTGTTTTTGTCAAACTAGAAACA
 P  P  L  F  V  S  N  V  A  Y  G  R  T  V  F  V  K  L  E  T 1270      1280      1290      1300      1310      1320
AGTTCTAAAAGTAATGATGTTGAAGCGGCCTTTAGTGCAGCTCTAAAAGGAACAGATGTT
 S  S  K  S  N  D  V  E  A  A  F  S  A  A  L  K  G  T  D  V 1330      1340      1350      1360      1370      1380
AAAACTAATGGAAAATACTCTGATATCTTAGAAAATAGCTCATTTACAGCTGTCGTTTTA
 K  T  N  G  K  Y  S  D  I  L  E  N  S  S  F  T  A  V  V  L 1390      1400      1410      1420      1430      1440
GGAGGAGATGCTGCAGAGCACAATAAGGTAGTCACAAAAGACTTTGATGTTATTAGAAAC
 G  G  D  A  A  E  H  N  K  V  V  T  K  D  F  D  V  I  R  N 1450      1460      1470      1480      1490      1500
GTTATCAAAGACAATGCTACCTTCAGTAGAAAAAACCCAGCTTATCCTATTTCATACACC
 V  I  K  D  N  A  T  F  S  R  K  N  P  A  Y  P  I  S  Y  T 1510      1520      1530      1540      1550      1560
AGTGTTTTTCCTTAAAAATAATAAAATTGCGGGTGTCAATAACAGAACTGAATACGTTGAA
 S  V  F  L  K  N  N  K  I  A  G  V  N  N  R  T  E  Y  V  E
```

FIG 2A-3

```
        1570      1580      1590      1600      1610      1620
ACAACATCTACCGAGTACACTAGTGGAAAAATTAACCTGTCTCATCAAGGCGCGTATGTT
  T  T  S  T  E  Y  T  S  G  K  I  N  L  S  H  Q  G  A  Y  V 1630      1640      1650      1660      1670      1680
GCTCAATATGAAATCCTTTGGGATGAAATCAATTATGATGACAAAGGAAAAGAAGTGATT
  A  Q  Y  E  I  L  W  D  E  I  N  Y  D  D  K  G  K  E  V  I 1690      1700      1710      1720      1730      1740
ACAAAACGACGTTGGGATAACAACTGGTATAGTAAGACATCACCATTTAGCACAGTTATC
  T  K  R  R  W  D  N  N  W  Y  S  K  T  S  P  F  S  T  V  I 1750      1760      1770      1780      1790      1800
CCACTAGGAGCTAATTCACGAAATATACGTATCATGGCTAGAGAGTGCACCGGCTTAGCT
  P  L  G  A  N  S  R  N  I  R  I  M  A  R  E [ C ] T  G  L  A 1810      1820      1830      1840      1850      1860
TGGGAATGGTGGCGAAAAGTGATCGACGAAAGAGATGTGAAACTGTCTAAAGAAATCAAT
  W  E  W  W  R  K  V  I  D  E  R  D  V  K  L  S  K  E  I  N 1870      1880      1890      1900      1910      1920
GTCAACATCTCAGGATCAACCCTGAGCCCATATGGTTCGATTACTTATAAGTAGGACTGG
  V  N  I  S  G  S  T  L  S  P  Y  G  S  I  T  Y  K

1930
TTCAAGAGGTTC
```

Fig.2(a).
The native, SLO.Cys.530.

Translated nucleotide sequence of native SLO gene.
The single Cys codon that was altered to generate
the active mutant described in Fig. 2(b), is
highlighted by the box.
Note: The numbering in the figure referrs to the
      nucleotide sequence.

FIG 2B-1

```
          10         20         30         40         50         60
TTATTAGCAAGCTTGCCATTTTATTTAAACCGTCAAAGCATACTAGCTAATATAACCAAA 70         80         90        100        110        120
GCGTTAAAAGATGCGCATTATTAGAGAGGCTATGGCACATTACAAATTAGGAGAATTTGC 130        140        150        160        170        180
TCACTATCAAGATACTATGCTTGATATGGTCGAAAGAACAATAGAAACATTTTAGAATGA 190        200        210        220        230        240
TAAAAGGTATGAAGGACATGTCTAATAAAAAAACATTTAAAAAATACAGTCGCGTCGCT
                    M   S   N   K   K   T   F   K   K   Y   S   R   V   A 250        260        270        280        290        300
GGGCTACTGACGGCAGCTCTTATCATTGGTAACCTTGTTACTGCTAATGCTGAATCGAAC
 G   L   L   T   A   A   L   I   I   G   N   L   V   T   A   N   A   E   S   N 310        320        330        340        350        360
AAACAAAACACTGCTAGTACAGAAACCACAACGACAAATGAGCAACCAAAGCCAGAAAGT
 K   Q   N   T   A   S   T   E   T   T   T   N   E   Q   P   K   P   E   S 370        380        390        400        410        420
AGTGAGCTAACTACTGAAAAAGCAGGTCAGAAAACGGATGATATGCTTAACTCTAACGAT
 S   E   L   T   T   E   K   A   G   Q   K   T   D   D   M   L   N   S   N   D 430        440        450        460        470        480
ATGATTAAGCTTGCTCCCAAAGAAATGCCACTAGAATCTGCAGAAAAAGAAGAAAAAAAG
 M   I   K   L   A   P   K   E   M   P   L   E   S   A   E   K   E   E   K   K 490        500        510        520        530        540
TCAGAAGACAAAAAAAAGAGCGAAGAAGATCACACTGAAGAAATCAATGACAAGATTTAT
 S   E   D   K   K   K   S   E   E   D   H   T   E   E   I   N   D   K   I   Y 550        560        570        580        590        600
TCACTAAATTATAATGAGCTTGAAGTACTTGCTAAAAATGGTGAAACCATTGAAAATTTT
 S   L   N   Y   N   E   L   E   V   L   A   K   N   G   E   T   I   E   N   F 610        620        630        640        650        660
GTTCCTAAAGAAGGCGTTAAGAAAGCTGATAAATTTATTGTCATTGAAAGAAAGAAAAAA
 V   P   K   E   G   V   K   K   A   D   K   F   I   V   I   E   R   K   K   K 670        680        690        700        710        720
AATATCAACACTACACCAGTCGATATTTCCATCATTGACTCTGTCACTGATAGGACCTAT
 N   I   N   T   T   P   V   D   I   S   I   I   D   S   V   T   D   R   T   Y 730        740        750        760        770        780
CCAGCAGCCCTTCAGCTGGCTAATAAAGGTTTTACCGAAAACAAACCAGACGCGGTAGTC
 P   A   A   L   Q   L   A   N   K   G   F   T   E   N   K   P   D   A   V   V
```

FIG 2B-2

```
       790        800        810        820        830        840
ACCAAGCGAAACCCACAAAAAATCCATATTGATTTACCAGGTATGGGAGACAAAGCAACG
 T   K   R   N   P   Q   K   I   H   I   D   L   P   G   M   G   D   K   A   T 850        860        870        880        890        900
GTTGAGGTCAATGACCCTACCTATGCCAATGTTTCAACAGCTATTGATAATCTTGTTAAC
 V   E   V   N   D   P   T   Y   A   N   V   S   T   A   I   D   N   L   V   N 910        920        930        940        950        960
CAATGGCATGATAATTATTCTGGTGGTAATACGCTTCCTGCCAGAACACAATATACTGAA
 Q   W   H   D   N   Y   S   G   G   N   T   L   P   A   R   T   Q   Y   T   E 970        980        990       1000       1010       1020
TCAATGGTATATTCTAAGTCACAGATTGAAGCAGCTCTAAATGTTAATAGCAAAATCTTA
 S   M   V   Y   S   K   S   Q   I   E   A   A   L   N   V   N   S   K   I   L 1030       1040       1050       1060       1070       1080
GATGGTACTTTAGGCATTGATTTCAAGTCGATTTCAAAAGGTGAAAAGAAGGTGATGATT
 D   G   T   L   G   I   D   F   K   S   I   S   K   G   E   K   K   V   M   I 1090       1100       1110       1120       1130       1140
GCAGCATACAAGCAAATTTTTTACACCGTATCAGCAAACCTTCCTAATAATCCTGCGGAT
 A   A   Y   K   Q   I   F   Y   T   V   S   A   N   L   P   N   N   P   A   D 1150       1160       1170       1180       1190       1200
GTGTTTGATAAATCAGTGACCTTTAAAGAGTTGCAACGAAAAGGTGTCAGCAATGAAGCT
 V   F   D   K   S   V   T   F   K   E   L   Q   R   K   G   V   S   N   E   A 1210       1220       1230       1240       1250       1260
CCGCCACTCTTTGTGAGTAACGTAGCCTATGGTCGAACTGTTTTTGTCAAACTAGAAACA
 P   P   L   F   V   S   N   V   A   Y   G   R   T   V   F   V   K   L   E   T 1270       1280       1290       1300       1310       1320
AGTTCTAAAAGTAATGATGTTGAAGCGGCCTTTAGTGCAGCTCTAAAAGGAACAGATGTT
 S   S   K   S   N   D   V   E   A   A   F   S   A   A   L   K   G   T   D   V 1330       1340       1350       1360       1370       1380
AAAACTAATGGAAAATACTCTGATATCTTAGAAAATAGCTCATTTACAGCTGTCGTTTTA
 K   T   N   G   K   Y   S   D   I   L   E   N   S   S   F   T   A   V   V   L 1390       1400       1410       1420       1430       1440
GGAGGAGATGCTGCAGAGCACAATAAGGTAGTCACAAAAGACTTTGATGTTATTAGAAAC
 G   G   D   A   A   E   H   N   K   V   V   T   K   D   F   D   V   I   R   N 1450       1460       1470       1480       1490       1500
GTTATCAAAGACAATGCTACCTTCAGTAGAAAAAACCCAGCTTATCCTATTTCATACACC
 V   I   K   D   N   A   T   F   S   R   K   N   P   A   Y   P   I   S   Y   T 1510       1520       1530       1540       1550       1560
AGTGTTTTCCTTAAAAATAATAAAATTGCGGGTGTCAATAACAGAACTGAATACGTTGAA
 S   V   F   L   K   N   N   K   I   A   G   V   N   N   R   T   E   Y   V   E
```

FIG 2B-3

```
        1570       1580       1590       1600       1610       1620
ACAACATCTACCGAGTACACTAGTGGAAAAATTAACCTGTCTCATCAAGGCGCGTATGTT
  T  T  S  T  E  Y  T  S  G  K  I  N  L  S  H  Q  G  A  Y  V 1630       1640       1650       1660       1670       1680
GCTCAATATGAAATCCTTTGGGATGAAATCAATTATGATGACAAAGGAAAAGAAGTGATT
  A  Q  Y  E  I  L  W  D  E  I  N  Y  D  D  K  G  K  E  V  I 1690       1700       1710       1720       1730       1740
ACAAAACGACGTTGGGATAACAACTGGTATAGTAAGACATCACCATTTAGCACAGTTATC
  T  K  R  R  W  D  N  N  W  Y  S  K  T  S  P  F  S  T  V  I 1750       1760       1770       1780       1790       1800
CCACTAGGAGCTAATTCACGAAATATACGTATCATGGCTAGAGGCCACCGGCTTAGCT
  P  L  G  A  N  S  R  N  I  R  I  M  A  R  E |A| T  G  L  A 1810       1820       1830       1840       1850       1860
TGGGAATGGTGGCGAAAAGTGATCGACGAAAGAGATGTGAAACTGTCTAAAGAAATCAAT
  W  E  W  W  R  K  V  I  D  E  R  D  V  K  L  S  K  E  I  N 1870       1880       1890       1900       1910       1920
GTCAACATCTCAGGATCAACCCTGAGCCCATATGGTTCGATTACTTATAAGTAGGACTGG
  V  N  I  S  G  S  T  L  S  P  Y  G  S  I  T  Y  K

1930
TTCAAGAGGTTC
```

Fig.2(b).
The active mutant, SLO.Ala.530.

Translated nucleotide sequence of the SLO.Ala.530 mutant gene. The mutant Ala codon, constructed by alteration of the native sequence described in Fig. 2(a), is highlighted by the box.

Note: The numbering in the figure, referrs to the nucleotide sequence.

STREPTOLYSIN O ANTIGEN DERIVATIVES, THEIR PRODUCTION AND USES

This is a continuation of application Ser. No. 07/959,167, filed Oct. 9, 1992, now abandoned, which is a continuation of application Ser. No. 07/830,549, filed Jan. 31, 1992, now abandoned, which is a continuation of application of Ser. No. 07/543,357 filed Jun. 25, 1990, now abandoned.

This invention relates to streptolysin O (SLO) antigens and their use, especially in diagnostic tests. In particular, the present invention relates to the identification, construction and production of cytolytic SLO derivatives. These derivatives do not contain any cysteine amino acids, but nevertheless they retain antigenic sites that can detect antibodies in serum samples. The invention also relates to use of these SLO derivatives in diagnostic anti-streptolysin O antibody tests (ASO tests), based on specific binding properties, such as binding between an antigen and an antibody and the inhibition of the cytolytic activities of SLO and cytolytic SLO derivatives by anti-SLO antibodies in human serum.

SLO is a toxic cytolytic protein produced by *Streptococcus pyogenes* (*S. pyogenes*) which causes a number of human diseases. During infection, the gene encoding SLO is expressed and SLO is secreted by *S. pyogenes*. The toxicity of SLO seems to be closely associated with its cytolytic activity. The SLO secreted by *S. pyogenes* is sensitive to oxidation and the cytolytic activity is greatly reduced after a period of exposure to air. This lost activity is restored by the addition of reducing agents such as dithiothreitol (DDT). The sensitivity of SLO to oxidation is associated with the presence of a cysteine amino acid in the native protein. Prior art indicates that this cysteine amino acid is an essential amino acid for the cytolytic activity of SLO. In this technical field, this cysteine amino acid is often referred to as the "essential cysteine".

The infected human host produces anti-SLO antibodies to antigenic sites on the SLO molecule. Thus diagnostic tests detecting these anti-SLO antibodies in human serum, can indicate (past or present) infection by *S. pyogenes*. The immunodiagnostic assays presently being used for detection of anti-SLO antibodies in human serum utilise active SLO protein prepared from cultures of *S. pyogenes*. These assays generally comprise the following steps:

(a) Take serum sample from patient.

(b) Make serial dilutions of serum sample in a suitable buffer.

(c) For each test include a control containing buffer, but no serum.

(d) Add a standard quantity of active SLO to each dilution of serum and to the control.

(e) Incubate the mixtures for a standard time and at a standard temperature, to allow any anti-SLO antibodies in the mixtures to combine with, and neutralise the added SLO.

(f) Add a standard quantity of red blood cells to each mixture.

(g) Incubate the mixtures for a standard time and at a standard temperature to allow any active (non-neutralised) SLO to lyse the added cells.

(h) Determine the highest dilution of serum that has neutralised the added SLO, that is which corresponds to the dilution producing less than 50% lysis of the added red blood cells.

Thus, where the serum sample contains high levels of anti-SLO antibody, there will be neutralisation of the active SLO up to a high dilution of the serum and therefore no lysis of the red blood cells. Conversely, where the serum sample does not contain antibodies to SLO, there will be no neutralisation and therefore there will be extensive lysis of red blood cells. Thus where the serum sample contains low levels of antibodies to SLO, there will be neutralisation only at low dilutions of the sample and there will be extensive lysis of the red blood cells at high dilutions of the sample.

However, there are a number of problems with preparing active SLO from *S. pyogenes* cultures for use in these assays, and, as stated, this protein is toxic and cytolytic and therefore laboratory facilities and trained personnel are required. The preparation of purified SLO from *S. pyogenes* is difficult and costly, particularly as SLO is sensitive to degradation by proteases that are secreted by *S. pyogenes*. Furthermore, SLO is sensitive to oxidation, due to the presence of a cysteine amino acid in the molecule. The gene encoding SLO has been cloned and expressed in *Escherichia coli* (*E.coli*) and the complete nucleotide sequence of the cloned SLO gene has been determined and the amino acid sequence of SLO has been deduced from the nucleotide sequence of the gene. These data have been published (Kehoe and Timmis, 1984, Infection and Immunity 43: 804–810 and Kehoe et al. 1987, Infection and Immunity 55: 3228–3232). These data showed that the SLO protein contains only one cysteine amino acid. The native SLO expressed by the cloned gene in *E. coli* could be used in the current immunodiagnostic assays. However, the cloned gene product also contains the cysteine amino acid. Prior art indicates that deletion of this single cysteine amino acid or the exchange of this cysteine amino acid for any other natural amino acid would irreversibly inactivate the cytolytic activity of SLO.

The problem addressed by the present application, was that of producing a cytolytic derivative of SLO which did not contain a cysteine amino acid and that was not sensitive to oxidation. It was not at all clear that this could be done.

The subject matter of the present application has been published by the applicants in Infection and Immunity, August 1989 p. 2553–2558. A similar publication in that same Journal reported similar findings in pneumolysin, see Infection and Immunity, August 1989 p. 2547–2552.

The present application provides data that shows that in SLO, the amino acid cysteine is not an essential amino acid for the cytolytic activity of SLO.

The present invention provides a DNA sequence encoding a cytolytic derivative of naturally occurring SLO that does not contain the amino acid cysteine. The present invention also provides recombinant vectors comprising such a DNA sequence and cells transformed with said recombinant vectors.

The present invention also provides a cytolytic derivative of naturally occurring SLO that does not contain the amino acid cysteine. Thus, in the cytolytic derivative of the thiol-activated SLO the derivative comprises at least one epitope immunologically cross-reactive with naturally occurring SLO and wherein the derivative comprises an amino acid sequence without the amino acid cysteine.

The derivative may be resistant to inactivation by oxidation or by chemical modification of a thiol group. In the cytolytic derivative, the cysteine residue of naturally occurring SLO may be substituted by a different amino acid. The different amino acid may be alanine or serine. The cytolytic derivative may comprise part or all of the amino acid sequence shown in FIG. 2b and wherein boxed alanine residue may be substituted by any amino acid other than cysteine.

The present invention also provides a process which comprises the production of an SLO derivative as previously described, by expression of the protein in a recombinant host cell from DNA encoding the derivative.

The present invention also provides a method of purifying anti-SLO antibodies, which comprises binding them to an SLO derivative as previously described.

The present invention also provides a method of raising anti-SLO antibodies, which comprises immunizing a subject with an SLO derivative as previously described.

The present invention also provides methods and diagnostic kits for detecting the presence or absence of antibodies to SLO in clinical samples, and for quantifying the levels of such antibodies in these samples. A typical diagnostic method may comprise replacing native SLO in the current ASO assays (described above) with the cytolytic SLO derivatives that do not contain a cysteine amino acid.

Thus, the present invention provides a diagnostic kit for detecting the presence or absence of antibodies to SLO in a clinical sample, which comprises an SLO derivative as previously described, together with ancillary components for detecting the binding of the derivative to anti-SLO antibodies in the sample.

The present invention also provides a method for detecting the presence or absence of antibodies to SLO in a clinical sample, which method comprises contacting the sample with an SLO derivative as previously described and measuring the cytolytic activity remaining after contact between the sample dilutions and said SLO derivative.

Figure 1:
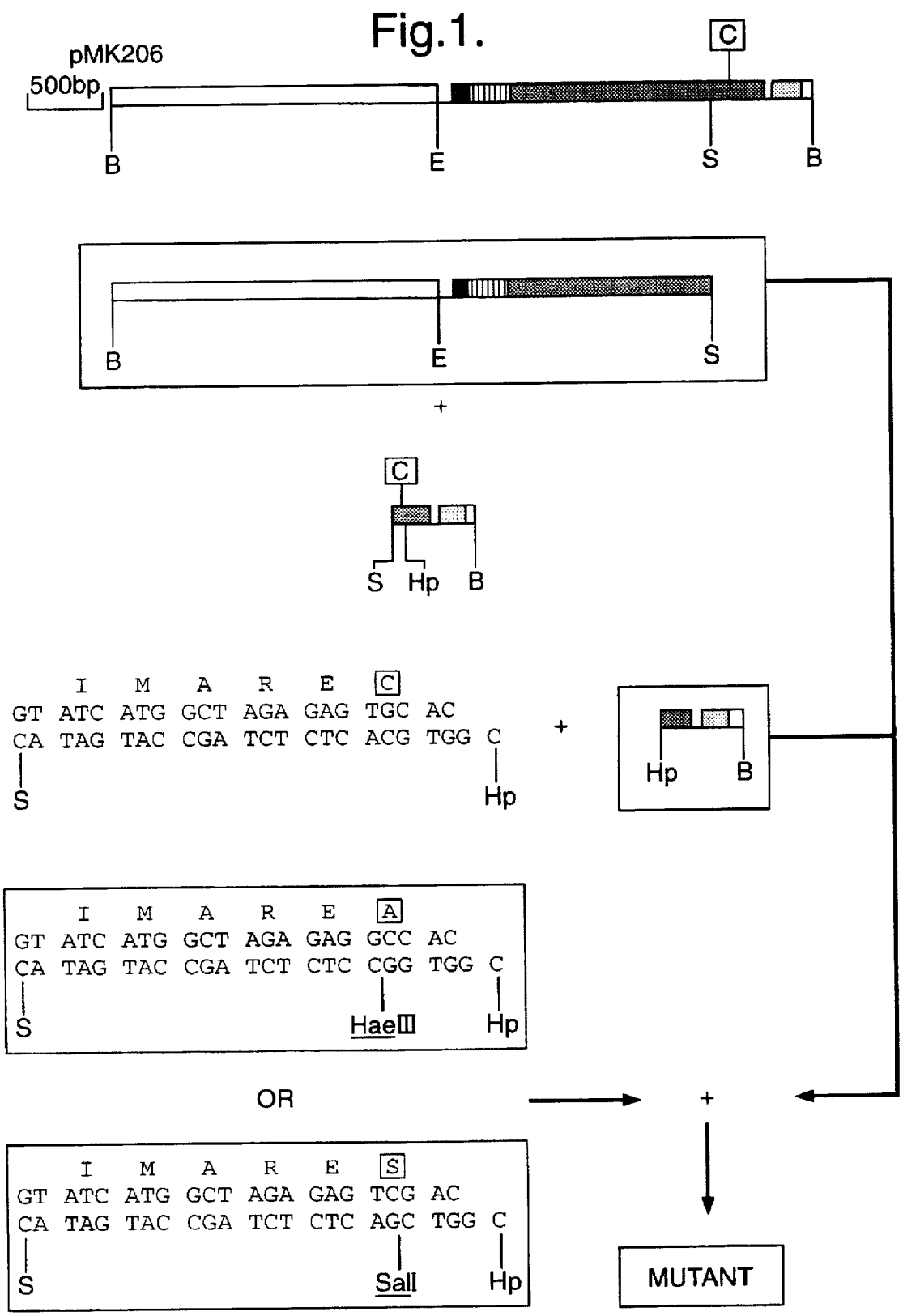
FIG. 1 shows the construction of mutant SLO genes encoding SLO derivatives that do not contain a cysteine amino acid.

FIG. 2(*a*) shows the complete nucleotide sequence of the native cloned SLO gene.

FIG. 2(*b* ) shows the complete nucleotide sequence of a mutant gene encoding a cytolytic SLO derivative that does not contain a cysteine amino acid.

In order that the present invention is more fully understood, embodiments will now be described by way of example only, but not by way of limitation, with reference to the Figures described above.

FIG. 1 shows the construction of mutant SLO genes encoding SLO derivatives that do not contain a cysteine amino acid. The structure of the $SLO^+$ hybrid plasmid, pMK206, is outlined at the top of the diagram, and the strategy used to construct the site-directed mutations is outlined below. In the line drawings, the blank boxes represent the vector DNA and the shaded boxes represent the SLO gene. The black box at the left end of the SLO gene corresponds to the predicted signal peptide, and the adjacent box (hatched) corresponds to the N-terminal sequences in the secreted high-molecular-weight form SLO, that are thought to be removed subsequent to secretion, to generate the low molecular weight form of the toxin (Kehoe, M. A., et al. (1987); Infect. Immun. 55:3228–3232). The single cysteine codon in SLO is indicated by the boxed C above the gene. The letters below the gene indicate cleavage sites for the following restriction endonucleases: B, BamHI; E, EcoRI; S, SnaBI; HP, HpaII. The approximate scale of the line drawings is indicated in the top left corner of the diagram. OL.Ala and OL.Ser describe the synthetic oligonucleotide linkers used to construct the mutants, and the restriction endonuclease fragments of pMK206 to which they were ligated are enclosed in boxes.

FIGS. 2A-1, 2A-2, 2A-3, 2B-1, 2B-2 and 2B-3 shows the complete nucleotide sequences of:

FIGS. 2A-1, 2A-2 and 2A-3 the native cloned SLO gene; and

FIGS. FIGS. 2B-1, 2B-2 and 2B-3 a mutant-gene encoding a cytolytic SLO derivative that does not contain a cysteine amino acid.

Detailed materials, methods and results are provided below but in summary, pMK206 DNA was cleaved with the restriction enzymes SnaBI (S) and BamHI (B) and the two resulting DNA fragments were separated by eleotrophoresis on agarose gels end purified (highlighted by boxes). The smaller of these two purified DNA fragments was then cleaved with the restriction enzyme HpaII (Hp) and the two resulting fragments were separated. The larger Hp-B fragment was purified and the smaller S-Hp fragment was discarded. A double stranded oligonucleotide was prepared by DNA synthesis in vitro and hybridisation, such that it replaced the discarded segment of the SLO gene with a new sequence that did not contain a cysteine amino acid codon, but that replaced this cysteine codon with a codon for an alanine or some other amino acid. The purified large B-S fragment from the first restriction enzyme cleavage, the purified Hp-B fragment from the second restriction enzyme cleavage and the synthetic double stranded oligonucleotides were ligated together to produce new plasmids. These new recombinant plasmids were transformed into an *E. coli* host end progeny expressing cytolytic SLO derivatives that do not contain a cysteine amino acid were identified. The sequence of one such derivative, where the cysteine codon is replaced by a codon for the amino acid alanine is shown in FIG. 2*b*. A procedure for producing the cytolytic SLO derivatives from the transformed *E. coli* cells has been developed such that protein that can be used in immunodiagnostic tests can be provided.

Bacterial Strains and Plasmids

*Escherichia coli* LE392 [F-hsdR514 supE44 supF58 lac Yl or Δ(lacIZY)6 galK2 galT22 metB1 trpR55η⁻] and JM103 [Δ(lac pro) thi strA supE endA sbcB hsdR (F'traD36 proAB $lacI^q$ lacZ ΔM15)], which were used as the hosts for recombinant plasmids and M13 phages, have been described by Maniatis et al (Maniatis, T., E. F. Fritsch, and J. Sambrook. 1982. Molecular cloning: a laboratory manual. Cold Spring Harbor Laboratory, Cold Spring Harbor, N.Y.) and Messing et al (Messing, J., R. Crea, and P. H. Seeburg, 1981; Nucleic Acids Res. 9:309–321). Phages M13mp18 and M13mp19 and the vector plasmid pUC18 have been described by Yanisch-Perron et al (Yanisch-Perron, C., J. Vieira, and J. Messing. 1985; Gene 33: 103–119). The construction of the $SLO^+$ hybrid plasmid, pMK157, has been described previously (Kehoe, M., and K. N. Timmis. 1984; Infect. Immun. 43:804–810). Growth conditions for *E. coli* strains and phages were as described previously (Kehoe, M., and K. N. Timmis. 1984, supra.; Leslie, D., N. Fairweather, D. Pickard, G. Dougan, and M. Kehoe. 1989; Mol. Microbiol. 3:383–392).

DNA Isolation, Cloning Sequencing and Synthesis Procedures

Restriction endonucleases, T4 DNA ligase, and DNA polymerase (Klenow) were obtained from CP Laboratories (Bishops Stortford, United Kingdom), NBL Ltd. (Cramlington, Northumberland, United Kingdom), or Amersham International (Amersham, United Kingdom) end were used according to manufacturer instructions. The procedures for plasmid or phage DNA purification, cloning, and sequencing have been described previously (Kehoe, M. A., L. Miller, J. A. Walker, and G. J. Boulnois. 1987, Infect. Immun. 55:3228–3232; Kehoe, M., and K. N. Timmis, 1984 supra.; Leslie. D., et al. 1989, supra.; Miller, L., V. Burdett, T. Poirier, E. Beachey, and M. Kehoe. 1988. Infect. Immun. 56: 2198–2204). Oligonucleotides were synthesized on an Applied Biosystems DNA Synthesizer (model 381A). Using reagents obtained from Applied Biosystems (Warrington, United Kingdom) and following the manufacturer's instructions. Before use, the purity of oligonucleotides was confirmed by electrophoresis on 20% (wt/vol) polyacrylamide gels, and if necessary the oligonucleotides were purified from the gel (Eperon, I. 1987; In G. J. Boulnois (ed), Gene cloning and analysis: a laboratory guide. Blackwell Scientific Publications Ltd. London).

Construction of a Stable, High-Copy-Number SLO$^+$ Plasmid, pMK206

The structure of the low-copy-number SLO$^+$ hybrid plasmid pMK157 and the nucleotide sequence of the cloned SLO gene have been described previously (Kehoe, M. A., et al. 1987, supra.; Kehoe, M., and K. N. Timmis. 1984, supra.). Previous attempts to clone the streptococcal DNA sequences from pMK157 into high-copy-number plasmid vectors failed due to detrimental effects on the host strain that rapidly selected for plasmids where the streptococcal sequences had been deleted (Kehoe, M., and K. N. Timmis, 1984; supra.). Plasmid pMK157 contains 6.2 kilobase pairs of cloned streptococcal DNA, and the SLO gene was located at one end of these sequences, within 50 base pairs (bp) of the vector-cloned DNA junction (Kehoe, M., and K. N. Timmis. 1984; supra.). In this study, a 2.0-kilobase-pair Fsp1-generated fragment from pMK157, containing the entire SLO gene and 115 bp of adjacent plasmid vector sequences, was cloned into the Sma1 site of pUC18 (Yanisch-Perron, C., et al. 1985; supra.) to produce a high-copy-number SLO$^+$ hybrid plasmid termed pMK206. The structure of pMK206 and the position of the single cysteine codon in the cloned SLO gene are shown in FIG. 1. The Fsp1 fragment cloned in pMK206 extends from 124 bp 5' to the SLO gene in pMK157 into vector sequences 165 bp beyond the 3' end of SLO. *E. coli* containing pMK206 expresses SLO at sufficient levels to facilitate its purification, though this expression is not controlled by the inducible pUC18 lac promoter. Cells containing pMK206 are stable, indicating that earlier stability problems were due to streptococcal sequences outside the SLO gene.

Construction of SLO Mutants

The procedure used to exchange the single cysteine codon (TGC) in SLO for other codons is outlined in FIG. 1. Digestion of pMK206 DNA with the restriction endonucleases SnaBI and BamHI generates two fragments, which were separated and purified by agarose gel electrophoresis. The single SLO TGC codon is located within 20 bp of the SnaBI-generated end of the smaller (322 bp) of these two fragments. HpaII, which produces 14 fragments on digesting pMK206 DNA, cleaves the small, 322-bp SnaBI-BamHI pMK206 fragment once, to generate a 22-bp SnaBI-HpaII fragment containing the TGC codon and a 300-bp HpaII-BamHI fragment containing the 3' end of SLO. These fragments were separated by gel electrophoresis, and the HpaII-BamHI fragment was recovered from the gel. Short double-stranded linkers, designed to replace the 22-bp SnaBI-HpaII fragment of pMK206, with sequences (synthetic oligonucleotide linkers incorporating the desired mutant codon) where the TGC codon was altered to GCC (Ala) or to TCG (Ser), were constructed by synthesizing and annealing complementary oligonucleotides. These linkers were designed so that the desired codon change would introduce a new restriction endonuclease cleavage site, in order to facilitate subsequent screening for mutants. These new sites are HaeIII in the case of the GCC (Ala) linker and SalI in the case of the TCG (Ser) linker. The large BamHI-SnaBI pMK206 fragment and the 300-bp HpaII-BamHI fragment were ligated with either the GCC (Ala) or the TCG (Ser) linkers to generate the pMK206 mutants pMK206.Ala-530 and pMK206.Ser-530. When the resulting mutant plasmids, pMK206.Ala-530 (Cys-530→Ala-530) and pMK206.Ser-530(Cys-530→Ser-530), were transformed into *E. coli* LE392 and transformants were selected on blood agar plates containing ampicillin, surprisingly, the majority of the transformants were hemolytic.

Peptide Synthesis and Antisera

Peptide SLOs[104–123], corresponding to residues 104 to 123 of the deduced SLO sequence (Kehoe, M. A., et al. 1987; supra.), was synthesized, and antipeptide antiserum was produced as described previously (Miller, L., et al. 1988; supra.).

Purification of SLO and its Mutant Derivatives

Wild-type SLO and its mutant derivatives, expressed from cloned genes in *E. coli* were purified using a procedure adapted from that of Bhakdi et al. (Bhakdi, S, M. Roth, A. Sziegoleit, and J. Tranum-Jensen. 1984; Infect. Immun. 46:394–400). Preliminary experiments showed that both the parent and mutant toxins can be released from *E. coli* by an osmotic shock procedure designed to release periplasmic proteins (Nossal, N. G., and L. A. Heppel. 1966; J. Biol. Chem. 241: 3055–3062), suggesting that they are located predominantly in the periplasm (data not shown), although this procedure was not efficient when scaled up for large culture volumes. For large-scale preparations, SLO was released from cells by a lysozyme-EDTA treatment that also resulted in a limited degree of cell lysis.

*E. coli* LE392, containing pMK206 or the mutant plasmids, was grown at 37° C., at 200 rpm to an $A_{600}$ of 1.0 in 7.5 liters of L broth supplemented with 100 µg of ampicillin per ml, and the cells were harvested by centrifugation at ca.10,000×g for 5 min.

All subsequent steps were carried out at 4° C. The cells were suspended in 300 ml of buffer A, which consisted of 25 mM Tris hydrochloride (pH 8.0) containing 50mM NaCl, 1 mM EDTA, 5% (vol/vol) glycerol, 2 mM phenylmethylsulfonyl fluoride, and 5 mM dithiothreitol. Lysozyme was added from a 1-mg/ml (in buffer A) stock solution to give a final concentration of 60 µg/ml. After 30 min, 30 ml of 250 mM EDTA (in buffer A) solution was added and the suspension was incubated for a further 15 min., followed by the removal of cells and cell debris by centrifugation at 16,000×g for 20 min. The supernatant was rapidly passed over a column (18 by 2.5 cm) of DEAE-Sephacel which had previously been equilibrated with buffer A. The column was washed with the same buffer, and SLO or its mutant derivatives, which did not bind to the column, were recovered in the wash eluent. After hemolytically active fractions were pooled, 25 g of solid polyethylene glycol 8000 per 100 ml was added and stirred slowly into solution. After a further 30 min. of stirring, the resulting precipitate was harvested by centrifugation at 18,000×g for 1 h. The pellets were carefully drained and suspended in 75 ml of buffer B (10 mM Tris hydrochloride [pH 9.0], 3 mM sodium azide, 1 mM dithiothreitol) containing 10 mM NaCl. This material was then loaded onto a DEAE-Sephacel column (12 by 2.5 cm) that had been pre-equilibrated with buffer B containing 10 mM NaCl. The column was washed with 80 ml of buffer B+10 mM NaCl and then with 20 ml of buffer B+50 mM NaCl, before elution with a linear salt gradient formed from 200 ml of buffer B+50 mM NaCl and 200 ml of buffer B+200 mM NaCl. Fractions containing hemolytic activity were identified and examined by sodium dodecyl sulfatepolyacrylamide gel electrophoresis (SDS-PAGE) (Laemmli, U.K., 1970; Nature (London) 227:680–685). Active fractions were combined according to their purity as judged by SDS-PAGE, dialyzed against buffer A, and then concentrated by ultrafiltration using a Filtron Technology Co. (Clinton, Mass.) ultrafiltration apparatus with a UF-polyethersulfone membrane, designed to retain globular proteins which have a molecular weight in excess of 50,000. A similar degree of purity was achieved with SLO and the mutant derivatives. The purified toxins were stored at −80° C. for up to 6 months without noticeable loss of activity or any effect on the stabilities of the high- and low-molecular-weight forms, as judged by SDS-PAGE. However, repeated freeze-thawing was found to be detrimental to the hemolytic activity and therefore the purified toxins were stored in small volumes.

Hemolytic Titration

The cytolytic activity of SLO and its mutant derivatives were measured by essaying hemolytic activity, essentially as described by Bhakdi et al (Bhakdi, S., et al. 1984; supra.). Human erythrocytes were washed three times with phosphate-buffered saline (0.137M NaCl, 2.7 mM KCl, 8.1 mM $Na_2HPO_4$, 1.5 mM $KH_2PO_4$ [pH 7.4]) and resuspended to a concentration of $2.5 \times 10^8$ erythrocytes per ml in phosphate-buffered saline. Titrations were performed in phosphate-buffered saline containing 0.5% (wt/vol) bovine serum albumin. A 50 µl volume of the erythrocyte suspension was added to 50 µl of serially diluted toxin (twofold dilutions) in 96-well microtiter plates, and after the plates were incubated for 30 min at 37° C., the wells corresponding to ca. 50% hemolysis were determined visually. The hemolytic titer was defined as the reciprocal of the highest dilution of toxin that produced >50% hemolysis. When required, cholesterol was added to the toxin diluent (phosphate-buffered saline) to a concentration of 5 µg/ml. Protein concentration was determined by the Bradford assay (Bradford, M. M. 1976; Anal. Biochem. 72: 248–254), and specific activity was defined as the number of hemolytic units per milligram of protein.

The specific hemolytic activity reported for the most highly purified preparations of SLO from S. pyogenes culture supernatants is 800,000 hemolytic units per mg of protein (Alouf, J. E. 1980; Pharm. Ther. 11:661–717; Bhakdi, S., et al. 1984; supra.). On SDS-PAGE, SLO purified from S. pyogenes culture supernatants resolves into a high-molecular-weight minor band and a lower-molecular-weight major band, and both forms have been shown to have identical specific hemolytic activities (Bhakdi, S., et al. 1984; supra.). Two similarly sized SLO antigens ($M_r$ 68,000 and $M_r$ 61,000) have been detected previously, by immunoblotting, in E. coli expressing the cloned gene (Kehoe, M., and K. N. Timmis. 1984; supra.) In this study, the recombinant wild-type SLO expressed in E. coli was purified to a specific hemolytic activity of 850,000 to 1,200,000 hemolytic unite per mg of protein, which is equivalent to the best preparations obtained from S. pyogenes culture supernatants (differences of up to twofold in the measured hemolytic activity were considered to be within the bounds of experimental error due to the nature of the assay).

The specific hemolytic activities of the purified wild-type SLO.CyS-530 and mutants SLO.Ala-530 and SLO.Ser-530 are described in Table 1. There were no significant differences in the specific hemolytic activities of wild-type SLO and the SLO.Ala-830 mutant, while the SLO.Ser-530 mutant had a reduced, but still considerable activity. Moreover, the cytolytic activities of all three toxins were equally inhibited by cholesterol (Table 1) or by neutralizing anti-SLO sera (data not shown). No differences were observed, during prolonged (6 months) storage, between wild-type and mutant toxins with respect to the stabilities of their specific hemolytic activities or the integrity of their high- and low-molecular-weight forms, as judged by SDS-PAGE.

TABLE 1

Specific hemolytic activities of SLO and the mutant toxins

| Purified toxin | Specific hemolytic activity[a] (HU/mg) | |
|---|---|---|
| | −Cholesterol | +Cholesterol[b] |
| SLO.Cys-530(wild type) | 850,000 | 3,000 (0.35) |
| SLO.Ala-530 | 750,000 | 3,000 (0.4) |
| SLO.Ser-530 | 200,000 | 700 (0.35) |

[a] A difference of up to twofold in the measured hemolytic activity is within the bounds of experimental error. HU, Hemolytic units.
[b] The figures in parentheses show the percentages of activity remaining in the presence of 5 µg of cholesterol per ml.

Oligomer Formation in Membranes and Isolation of SLO Oligomers

Toxins such as SLO band to cholesterol-containing membranes in e temperature-independent manner and oligomerize in the membrane in a temperature-dependent manner to form large arc- and ring-shaped structures composed of 25 to 100 toxin monomers (Alouf, J. E. 1980, supra.; Bhakdi, S., and J. Tranum-Jensen. 1986, Microb. Pathogen. 1:5–14; Bhakdi, S., J. Tranum-Jensen, and A. Sziegoleit. 1985, Infect. Immun. 47: 52–60; Duncan, J. L., and R. Schlagel. 1975, J. Cell. Biol. 67:160–173). Once formed, the oligomers appear to be quite stable, and intact oligomers have been isolated by gentle solubilization of lysed erythrocyte membranes (Bhakdi, S., et al. 1985; supra.). Isolated oligomers have been shown not to contain detectable quantities of cholesterol, but they can insert into cholesterol-free liposomes, suggesting that cholesterol may be required only for the initial stages in the cytolytic process (Bhakdi, S., et al. 1985; supra.). Although the role of these toxin oligomers in membrane disruption has not been clearly established, freeze-fracture studies suggest that they span the membrane and, concomitant with their formation, high-molecular-weight cytoplasmic molecules leak from the cell, resulting in cell death (Alouf, J. E. 1980, supra.; Bernheimer, A. W. 1974; Biochim. Biophys. Acta 344:27–50; Bernheimer, A. W. 1977; In A. W. Bernheimer (ed.). Mechanisms in bacterial toxinology. John Wiley & Sons. Inc., New York; Bhakdi, S., et al. 1986, supra.; Duncan, J. L. et al. 1975, supra.; Smyth, C. J., and J. L. Duncan, 1978, In J. Jeljaszewicz and T. Wadstrom (ed). Bacterial toxins and cell membranes. Academic Press. Inc. (London). Ltd., London).

To determine the abilities of the mutant toxins to form oligomers in membranes, human erythrocyte membranes from cells that had been lysed with SLO or the mutant toxins were extracted gently with 250 mM sodium deoxycholate and fractionated on sucrose density gradients, as described by Bhakdi et al (Bhakdi et al, 1985; supra.). Membranes from osmotically lysed erythrocytes and purified toxins treated with deoxycholate in the gradient loading buffer (no membranes) were included as controls. Gradient fractions were analyzed by SDS-PAGE and immunoblotting with a monospecific anti-SLO peptide (SLO.s[104–123]) antiserum as the primary antibody and with peroxidase-conjugated sheep anti-rabbit immunoglobulin (sera-lab. Ltd., Sussex, United Kingdom) as previously described (Leslie et al, 1989; supra.). In the absence of membranes, the wild-type SLO.Cys-530 and both the SLO.Ala-530 and SLO.Ser-530 mutant toxins were detected in low-density fractions, whereas, in each case, toxin extracted from lysed cell membranes sedimented into high-density fractions. This result is identical to that previously obtained using SLO purified from *S. pyogenes* culture supernatants by Bhakdi et al (Bhakdi et al, 1985; supra.)., who demonstrated that SLO in the high-density fractions was in the form of oligomers corresponding to the typical arc- and ring-shaped structures observed in SLO-treated membranes by electron microscopy. This suggests that the cysteine residue in SLO is not essential for oligomer formation.

Effect of Thiol-Blocking Agents on Native and Mutant Toxin Activities

Iodoacetamide and para-hydroxymecuribenzoic acid (PHMB) are examples of agents which interact with the thiol-groups of cysteine amino acids in proteins. Prior art had shown that such agents inhibit the activity of native SLO isolated from *S. pyogenes* and this was interpreted as indicating that native SLO contains one or more "essential cysteine" amino acids (Van Epps D. E. and Anderson B. R. 1971 Infect. Immun. Vol. 3, p.648–652. Alouf, J. E.; supra.). The invention described in this application shows that this conclusion is not correct. To determine whether this mistake was due to faulty experimental date or to the obvious interpretation from the experimental data being incorrect, the effects of iodoacetamide and PHMB on the cytolytic activities of native (SLO.Cys.530) and the mutant (SLO.Ala.530 end SLO.Ser.530) toxins was examined (Table 2). The data showed that iodoacetamide and PHMB do inhibit the cytolytic activity of the native SLO.Cys.530, but that they have no significant effect on the cytolytic activities of the SLO.Ala.530 and SLO.Ser.530 mutant toxins. This indicates that the inhibitory effect of these agents of the native toxin is, as suggested by prior art, due to their interaction with the cysteine amino acid. However, as the invention described in this application shows, the obvious conclusion from this data that cysteine is essential for activity is, surprisingly, not correct. This apparent contradiction can be understood by postulating that the cysteine amino acid in native SLO is located in e region of the toxin which is important for activity and, while the cysteine amino acid itself is not essential for activity, the interaction of external agents with the cysteine may hinder, for example by static hinderance, the functions of adjacent regions of the molecule.

Effect of iodoacetamide and PHMB on toxin activity

| | Specific hemolytic activity (HU/mg) | | |
|---|---|---|---|
| | SLO.Cys.530 (native) | SLO.Ala.530 | SLO.Ser.530 |
| Toxin alone | 850,000 | 750,000 | 200,000 |
| Toxin +: | | | |
| Iodoacetamide | 0 | 550,000 | 200,000 |
| PHMB | 25,000 | 750,000 | 400,000 |

We claim:

1. A cytolytic derivative of the protein streptolysin O (SLO) immunologically cross-reactive with naturally occurring streptolysin O wherein Cys-530 of naturally occurring SLO has been substituted by a different amino acid.

2. A cytolytic derivative according to claim 1 which is resistant to inactivation by oxidation or by chemical modification of a thiol group.

3. A cytolytic derivative according to claim 1 wherein the different amino acid is alanine.

4. A cytolytic derivative according to claim 1 which comprises part of the amino acid sequence shown in FIG. 2B-1, 2B-2 and 2B-3 and wherein said boxed alanine residue may be substituted by any amino acid other than cysteine.

5. A process which comprises the production of a cytolytic derivative of the protein streptolysin O (SLO) immunologically cross-reactive with naturally occurring SLO wherein Cys-530 of naturally occurring SLO has been substituted by a different amino acid by expression of the cytolytic derivative in a recombinant host cell from DNA encoding the cytolytic derivative.

6. A method of purifying anti-streptolysin O antibodies which comprises binding them to a cytolytic derivative of the protein streptolysin O (SLO) immunologically cross-reactive with naturally occurring SLO wherein Cys-530 of naturally occurring SLO has been substituted by a different amino acid.

7. A method of raising anti-streptolysin O antibodies which comprises immunizing a subject with a cytolytic derivative of the protein streptolysin O (SLO) immunologically cross-reactive with naturally occurring SLO wherein Cys-530 of naturally occurring SLO has been substituted by a different amino acid.

8. A diagnostic kit for detecting the presence or absence of antibodies to streptolysin O (SLO) in a clinical sample, which comprises a cytolytic derivative of SLO immunologically cross-reactive with naturally occurring SLO wherein Cys-530 of naturally occurring SLO has been substituted by a different amino acid together with ancillary components for detecting the binding of the derivative to anti-SLO antibodies in the sample.

9. A method for detecting the presence or absence of antibodies to streptolysin O (SLO) in a clinical sample, which method comprises contacting the sample with a cytolytic derivative of SLO immunologically cross-reactive with naturally occurring SLO wherein Cys-530 of naturally occurring SLO has been substituted by a different amino acid, and measuring the cytolytic activity remaining after contact between the sample and said cytolytic derivative.

10. A cytolytic derivative according to claim 1 that has the sequence depicted in FIGS. 2B-1, 2B-2 and 2B-3.

11. A cytolytic derivative according to claim 1 that has a serine at position 530.

12. A cytolytic derivative according to claim 1, wherein said streptolysin O (SLO) has the sequence depicted in FIGS. 2A-1, 2A-2 and 2A-3.

13. A streptolysin O (SLO) protein derivative lacking the cysteine residue at position 530 of wild-type SLO, but retaining SLO cytolytic activity, wherein said activity is inhibited by neutralizing anti-SLO antiserum.

14. A streptolysin O (SLO) derivative lacking the cysteine residue at position 530 of wild-type SLO, but retaining SLO cytolytic activity, wherein said activity is inhibited by cholesterol.

15. A cytolytic derivative of streptolysin O (SLO), wherein the SLO has the sequence depicted in FIGS. 2A-1, 2A-2 and 2A-3, wherein at least the cysteine residue at position 530 has been substituted by a different amino acid.

16. A method for making a cytolytic derivative of streptolysine O (SLO) comprising substituting at least the codon for the cysteine at position 530 of the naturally occurring SLO of FIGS. 2A-1, 2A-2 and 2A-3 with a codon encoding a different amino acid.

* * * * *